United States Patent
Ringeisen

(10) Patent No.: US 8,679,164 B2
(45) Date of Patent: Mar. 25, 2014

(54) COMPLIANT OSTEOSYNTHESIS FIXATION PLATE

(75) Inventor: Timothy A. Ringeisen, Exton, PA (US)

(73) Assignee: Kensey Nash Corporation, Exton, PA (US)

( * ) Notice: Subject to any disclaimer, the term of this patent is extended or adjusted under 35 U.S.C. 154(b) by 265 days.

(21) Appl. No.: 13/094,673

(22) Filed: Apr. 26, 2011

(65) Prior Publication Data

US 2011/0218634 A1     Sep. 8, 2011

Related U.S. Application Data

(63) Continuation of application No. 10/619,721, filed on Jul. 15, 2003, now Pat. No. 7,931,695.

(51) Int. Cl.
A61F 2/28     (2006.01)

(52) U.S. Cl.
USPC .......................................................... 606/284

(58) Field of Classification Search
USPC ......... 606/280, 70, 283–286, 298–300, 86 R;
623/11.11, 23.51, 23.57, 23.58, 23.61,
623/23.72, 23.75
See application file for complete search history.

(56) References Cited

U.S. PATENT DOCUMENTS

| | | | |
|---|---|---|---|
| 3,739,773 A | 6/1973 | Schmitt et al. |
| 3,741,205 A | 6/1973 | Markolf et al. |
| 3,877,424 A | 4/1975 | Murray |
| 4,186,448 A | 2/1980 | Brekke |
| 4,920,203 A | 4/1990 | Tang et al. |
| 4,966,599 A | 10/1990 | Pollock |
| 5,201,733 A | 4/1993 | Etheredge, III |
| 5,290,281 A | 3/1994 | Tschakaloff |
| 5,413,577 A | 5/1995 | Pollock |
| 5,855,608 A | 1/1999 | Brekke et al. |
| 5,948,020 A | 9/1999 | Yoon et al. |
| 6,031,148 A | 2/2000 | Hayes et al. |
| 6,203,573 B1 | 3/2001 | Walter et al. |
| 6,221,075 B1 | 4/2001 | Tormala et al. |
| 6,306,424 B1 | 10/2001 | Vyakarnam et al. |
| 6,332,884 B1 | 12/2001 | Cooper |
| 6,336,930 B1 | 1/2002 | Stalcup et al. |

(Continued)

FOREIGN PATENT DOCUMENTS

| EP | 0274898 A2 | 7/1988 |
|---|---|---|
| EP | 0784985 A1 | 7/1997 |

(Continued)

*Primary Examiner* — Pedro Philogene
*Assistant Examiner* — David Comstock
(74) *Attorney, Agent, or Firm* — Jeffrey R. Ramberg

(57) ABSTRACT

A bendable polymer tissue fixation device suitable to be implanted into a living body, comprising a highly porous body, the porous body comprising a polymer, the porous body comprising a plurality of pores, the porous body being capable of being smoothly bent, wherein the bending collapses a portion of the pores to form a radius curve, the polymer fixation device being rigid enough to protect a tissue from shifting. In a preferred embodiment the polymer fixation device may be capable of being gradually resorbed by said living body. In one embodiment, the polymer fixation device comprises a plurality of layers distinguishable by various characteristics, such as structural or chemical properties. In another embodiment, the polymer fixation device may comprise additional materials; the additional materials serving to reinforce or otherwise alter the structure or physical characteristics of the device, or alternatively as a method of delivering therapy or other agents to the system of a living being.

30 Claims, 9 Drawing Sheets

(56) References Cited

U.S. PATENT DOCUMENTS

| | | |
|---|---|---|
| 6,344,042 B1 | 2/2002 | Curtis et al. |
| 6,391,059 B1 | 5/2002 | Lemperle et al. |
| 6,454,770 B1 | 9/2002 | Klaue |
| 7,235,107 B2 | 6/2007 | Evans et al. |
| 7,931,695 B2 * | 4/2011 | Ringeisen .................. 623/23.72 |
| 2002/0127265 A1 | 9/2002 | Bowman et al. |

FOREIGN PATENT DOCUMENTS

| | | |
|---|---|---|
| EP | 1064958 A1 | 1/2001 |
| EP | 1216718 A1 | 6/2002 |
| EP | 0562864 A1 | 9/2003 |
| WO | WO-86/00533 A1 | 1/1986 |
| WO | WO-99/56800 A1 | 11/1999 |
| WO | WO-2004/006973 A1 | 1/2004 |

* cited by examiner

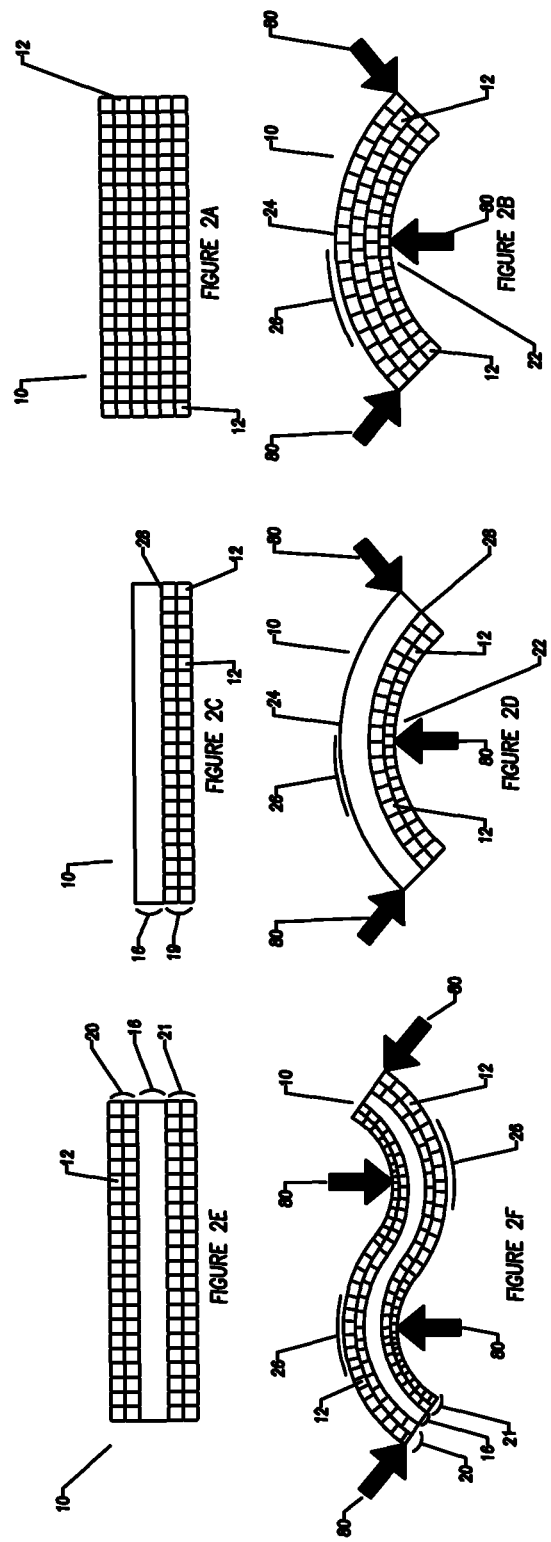

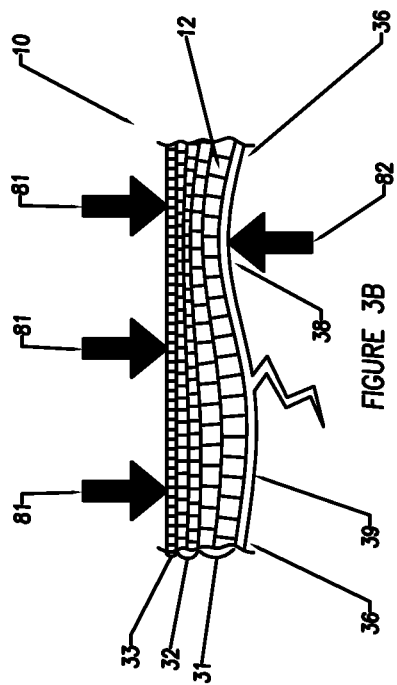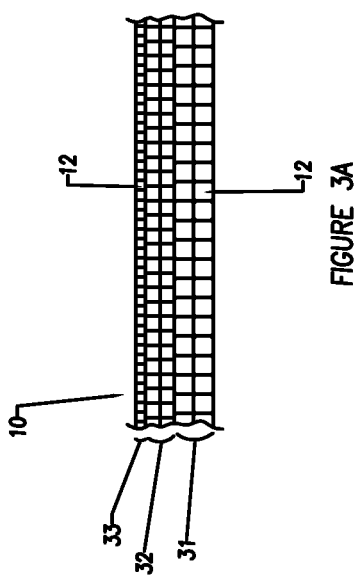

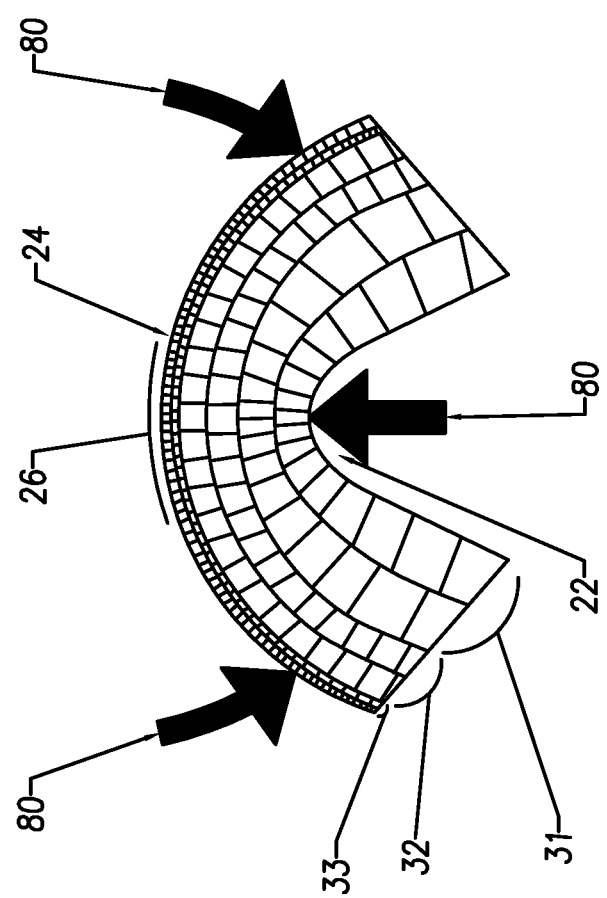

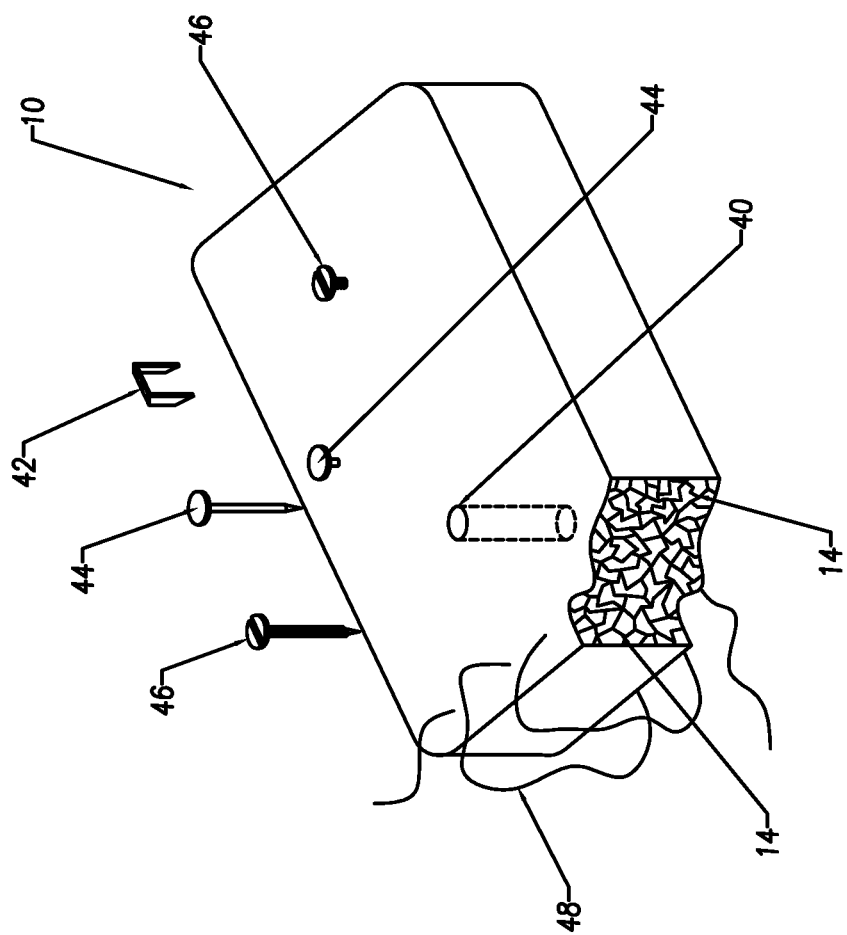

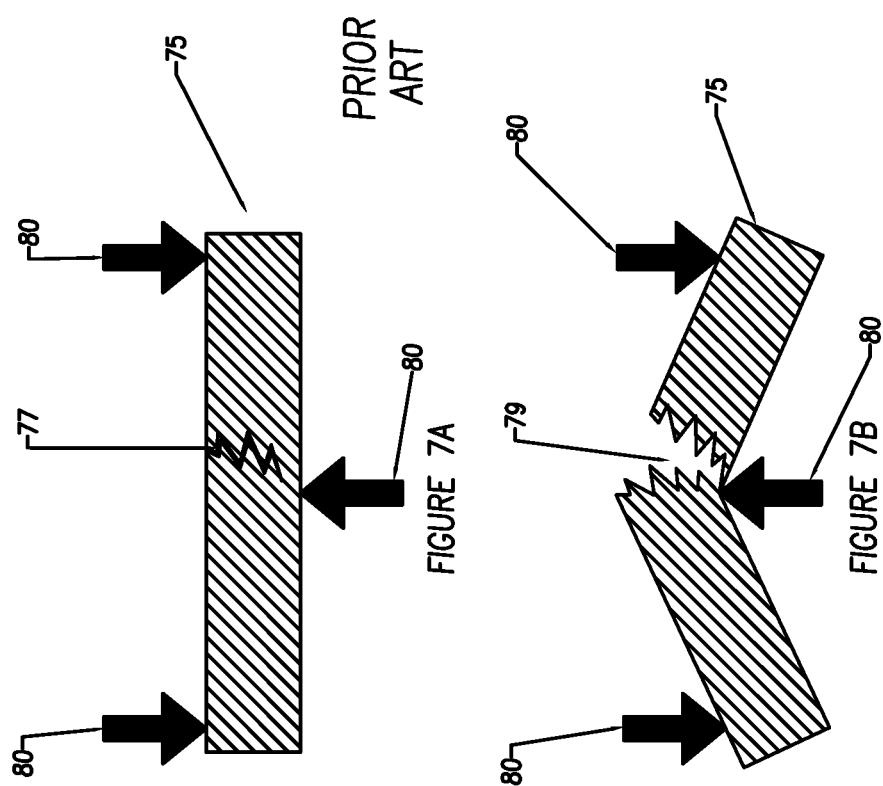

COMPLIANT OSTEOSYNTHESIS FIXATION PLATE

CROSS-REFERENCE TO RELATED APPLICATIONS

This application is a Continuation of U.S. patent application Ser. No. 10/619,721, filed on Jul. 15, 2003, now U.S. Pat. No. 7,931,695 entitled Compliant Osteosynthesis Fixation Plate which is assigned to the same assignee as this invention, and whose disclosure is incorporated by reference herein.

FIELD OF THE INVENTION

The invention generally relates to prosthetic implants, specifically relating to resorbable prosthetic implants. The invention more particularly concerns a resorbable osteosynthesis fixation plate. Specifically, an implant for joining tissue or bone fragments of the cranium, face and other plastic/reconstructive procedures.

BACKGROUND OF THE INVENTION

Rigid internal fixation has been indicated for treatment of defects of the mammalian skeletal system for decades. Although external fixation such as plaster and splints have been used to stabilize the skeleton since ancient times, it was not until the emergence of steel wire in the nineteenth century that a practical method for treating non-isolatable bone fragments such as those found in craniomaxillofacial repair situations was developed.

A great advancement in skeletal fixation occurred in the late 1950s with the introduction of metallic plate systems. By securing the plate to the individual bone components with screws, this relatively simple device prevented fragment motility commonly encountered with wire-stabilized repair. These plates are generally sheets of metal that are fenestrated at various points along their lengths for fastening by screw. Over the years, metallic plate systems have become miniaturized and more biocompatible. Initially made from stainless steel, subsequent alloys, which include Vitallium® and titanium, were developed allowing for improved strength and rigidity. A panoply of geometric configurations is available to meet nearly every conceivable bone fixation need. The application of metallic materials has greatly improved aesthetic outcomes and has enabled earlier and more complete surgical reconstructions.

The search for improved fixation implants has lead to the development of a plethora of prostheses for utilization in surgical procedures, for example, fiber reinforced sheets to prevent hernias, bone plates to allow healing of bones after fracture and skull plates for use after cranial surgery. In particular, bone fixation plate and skull plate implants are utilized in a manner such that their placement may prevent bone fragment movement relative to the remainder of the bone. See, e.g., U.S. Pat. No. 3,741,205. The construction of these prostheses has historically been of some metal or metal alloy, e.g., surgical stainless steel, titanium, or Vitallium®. See, e.g., U.S. Pat. No. 6,344,042. These metal prostheses have the desired strength and rigidity to properly stabilize the area and allow the healing process to occur unimpeded by fragment and/or bone shifting. The stabilization may be external to the body, by use of a scaffold of rods and braces (see, e.g., U.S. Pat. No. 3,877,424) or alternatively, implanted internally and fastened to the bone via a securing means, such as cementing, medical staples, pins, nails, tacks, screws or clamps. See, e.g., U.S. Pat. Nos. 5,201,733; 6,454,770; 6,336,930.

Metal plates to be utilized as prostheses to immobilize bone fragments have the ability to be customized to fit the unique contours of each patient. Customization of the prosthesis is accomplished by twisting and bending the plates to fit the surgical site. Despite the utility of metallic plate systems, their use is not without problems. Multiple bending attempts may be required to achieve a desired fit, potentially fatiguing the metal. Furthermore, an extended customization and shaping process may lead to higher risk for the patient, due to a protracted period while under anesthesia, as well as increased opportunity for infection.

The consequences of long-term metal implants over a fifty to seventy year period are not known. Particles from these devices have been isolated in very distant organs such as the liver and the lung. Trace amounts of aluminum and nickel have been found in tissues surrounding implants thought to be composed of pure titanium. Metal plates have the drawback of remaining in place long after the healing process is complete, unless removed through a second invasive procedure. This intransience may be harmful where there is a need for continued bone growth and that growth is restrained by the implant, e.g., a child's skull must be capable of continued growth through development, and a metal skull plate, if left in place after cranial surgery, would interfere with developmental growth. Other postoperative complications from metallic plating systems include: visibility or palpability, hardware loosening with resulting extrusion (e.g. "screw backout"), temperature sensitivity to cold, screw migration and maxillary sinusitis, bone atrophy or osteopenia caused by stress shielding and corrosion, interference with radiographic imaging and radiation therapy, allergic reactions, intracranial migration in cranio-orbital surgery, and the possibility of causing growth restriction of the craniofacial skeleton on pediatric patients. Additionally, a metal prosthesis, if not removed after healing, may over time corrode or allow the leaching of metals to other locations of the body. For these reasons, the pursuit of other fixation technology has continued.

In order to overcome some or all of the drawbacks of metal implants, considerable attention has been given to the field of biodegradable (absorbable, resorbable) prostheses. These prostheses are capable of protecting the injury site, while still allowing the healing process to occur; however the resorbable nature of the prostheses allows the prostheses to remain in place only as long as would be needed to complete the healing process. The resorption of the implant obviates the need for a second surgical procedure to remove the implant, as might be required for a non-absorbable prosthesis, thereby reducing opportunity for infection or other complications. Additionally, any problems commonly associated with metal implants that may also be associated with resorbable implants, such as bone atrophy, would be transient, as the problem would not persist beyond the absorption of the implant.

The use of resorbable materials to form an implantable prosthesis is not new. See, e.g., U.S. Pat. No. 3,739,773. Bioresorbable internal fixation devices have been available for years principally as pins, plugs, screws, tacks and suture anchors. In 1996, the United States Food and Drug Administration approved the first bioresorbable internal fixation system for craniomaxillofacial indications (LactoSorb®, Walter Lorenz Surgical, Inc., Jacksonville, Fla.). Available in a variety of screws, panels and plate designs, the material is a non-porous amorphous copolymer of L-lactic and glycolic acid in a ratio of 82:18 and engineered to completely resorb in 9 to 15 months following placement. The material has manufactured fenestration points located throughout the device to allow for screw fixation to bone. Other resorbable materials now available commercially include Synthes® and MacroPoreFX™ fixation plates.

Prior art discloses that bioresorbable internal fixation plates can be manufactured by injection molding or compression molding techniques. For injection molding, a mold of the desired plate is first fabricated. The desired polymer is then heated significantly above its glass transition temperature until its viscosity is low enough to allow the polymer to flow. As this is occurring, a screw carries the molten polymer into the mold where it is allowed to cool below its glass transition temperature. The polymer is now solidified to the shape of the mold. The advantage to injection molding is that extremely intricate mold designs can be produced. One disadvantage of injection molding, however, is that the polymer may undergo a relatively long heat cycle, which breaks down the molecular weight of the polymer, thereby, affecting material strength as well as degradation characteristics. Another major disadvantage to injection molding is that there will usually be a certain amount of inherent stress within the plate due to freezing the polymer in place prior to it obtaining the orientation of lowest energy. Over time, or if the plate is heated prior to use, it will deform in order to relieve the stress in the part. In the case of heat application, the screw holes of the plate have been shown to become distorted causing some screw points to become unusable or preventing proper thread contact and alignment. Annealing may be used to help prevent this deformation from occurring Annealing requires holding the plate in place while heating it above its glass transition temperature and waiting for the stress to relieve. This is an additional heating step and can lengthen a manufacturing process or further break down the molecular weight of the polymer.

Another method of thermally forming a polymer into a resorbable fixation plate is compression molding. Under this method, a mold is first produced and placed between hot platens. The two mold halves are separated and polymer is placed into the mold. Compressive pressure is applied to the mold and it is then heated above the glass transition temperature of the polymer. The polymer will eventually start to flow as the mold heats up and the material will take the shape of the mold. The advantage to this method is that the fixation plates incur very little molded-in stress because the polymer only has a relatively short distance to move. Disadvantages to this method include an even longer heating cycle than injection molding, a slow process that is difficult to use on a large scale, and a process that may require machining the holes into the fixation plate as a second operation.

The materials derived from ordinary thermal molding techniques (injection and compression molding) are not flexible at room temperature. Generally, the resorbable craniomaxillofacial products currently on the market are not deformable at room temperature and must be heated prior to implantation to adapt the device to the contours of the wound site. As the patients often vary in size, and because the bone surfaces are not flat, during implantation there exists a need to fit the prosthesis to the particular contours of each patient. Various techniques may be utilized to heat the prosthesis (e.g. exposure to hot air, immersion in hot liquid, exposure to radiation or exposure to some other heating medium) to a temperature above the glass transition point, but below the melting point; thereby making the prosthesis temporarily flexible, and allowing it to be fitted to an individual by bending, either by hand or with special bending tools. See, e.g., U.S. Pat. No. 5,290,281. After heating, the physician has only a limited amount of time, often just seconds, in which to accomplish the bending. Depending on the thickness of the plate, this period of malleability can be as short as two to three seconds causing the practitioner in many instances to expend considerable time to reheat and reshape the material several times while bending to achieve proper conformity. This additional time increases anesthesia requirements and operating room time and increases the potential of infection. See U.S. Pat. No. 6,332,884 for a prosthesis that turns to a clear solid while heated above its glass transition temperature, and reverts back to an opaque solid when cooled below the glass transition temperature, giving a visual indication to the physician about the status of the prosthesis' flexibility. The limited period of time available for bending of the prosthesis requires dexterity and care by the physician to create a shape that is adequate for use with each individual. The repeated heating, if necessary, to allow careful molding of the prosthesis adds to the time and complexity and cost of the procedure, further increasing the risk to the patient. Furthermore, if the prosthesis is not properly heated above the glass transition temperature as required for flexibility, and is bent while below the glass transition temperature, then the prosthesis will remain inflexible or be rather brittle, and likely develop cracks and/or micro-cracks upon bending.

In U.S. Pat. No. 6,221,075, there is disclosed a polymer tissue fixation device that may be deformed at room temperature. The ability of the polymer to be deformed without heating is made possible by an additional manufacturing step incorporated into the thermal molding techniques described above, where the polymer material is oriented with an uni- and/or biaxial solid state deformation process. The solid state deformation process orients the molecules of the polymer, so that room temperature bending is possible without substantial damage or breaking. The deformation process adds to the cost of manufacturing the tissue fixation device, adding to required labor and time of manufacture. In order to avoid unwanted bending or warping of the device while exposed to temperatures above the glass transition point but below the melting point, the device must be maintained at elevated temperature after deformation to allow stress relief of the polymer molecules. After the deformation step or stress relief step, any further modifications or machining, such as holes for fastening devices, must be created before use, such as by drilling.

Walter et al. in U.S. Pat. No. 6,203,573, disclose molded, biodegradable porous polymeric implant materials having a uniform pore size distribution. The materials can be molded into implants of any desired size and shape without loss of uniformity of pore size distribution. The material may be hand-shaped when warmed to body temperatures, and more preferably when warmed to at least about 45 degree C. and more preferably to at least about 50 degree C. Once at an elevated temperature, the implant material can be further hand-shaped to fit the defect into which they are placed and the desired shape for the regrown tissue.

A need, therefore exists for an internal fixation device that can be resorbed by the body over time, yet provide sufficient strength to prevent bone fragment motility over the healing period necessary for natural repair. Furthermore, the device must be capable of manual deformation at room temperature to fit the unique shape of each individual patient without the use of heat or chemical manipulation, wherein the deformation may occur by bending or application of a compressive force. Also the device must be capable of resisting the formation of micro-cracks caused by shaping, or distortions caused by the introduction of fastening techniques known in the art.

A prosthesis as described above would have the benefits of ease of use in surgery, along with the associated benefit for the patient of reducing the total time under anesthesia, and minimizing the risk of infection for the patient.

In U.S. Pat. Nos. 4,966,599 and 5,413,577, Pollock discloses a set of pre-formed bone plates, to be manufactured as a kit. The use of an individual bone plate, comprising one of many in the kit, will still require final shaping by bending or crimping of the plates while the patient is undergoing surgery. Pollock has taken an approach to minimize the amount of time required to customize the implant by manufacturing many plates, encompassing a plurality of generic shapes and sizes, such that only minor customization by bending of the appropriate prosthesis would be required. A multi-piece kit, such as described by Pollock, would necessarily result in waste as the unused sizes and shapes of the kit would be discarded as not being appropriate for the specific patient's needs.

In U.S. Pat. No. 4,186,448, Brekke describes the use of a porous body, made of biodegradable material, to fill or cover a bone void. This material includes interconnected, randomly positioned, randomly shaped and randomly sized voids extending throughout the mass of the body member. The voids promote the penetration of blood into the prosthesis and aid healing through the facilitation of tissue and/or bone growth into the prosthesis. The prosthesis as described promotes tissue ingrowth and is replaced by new bone upon resorption.

The use of a resorbable prosthesis that serves as a barrier to cell permeability, while allowing bone wound or void healing is disclosed by Hayes et al. in U.S. Pat. No. 6,031,148, and also by Brekke et al. in U.S. Pat. No. 5,855,608. Hayes' prosthetic material serves as a pliable barrier to cells, acting to prevent soft tissue growth in areas where bone growth is desired. The Hayes patent discloses the pliable prosthesis having a matrix that is sufficiently open to allow infiltration of blood and subsequent interconnection of ingrowing tissue through the open spaces. Brekke discloses a resorbable implant that is capable of serving as a barrier to isolate one form of tissue (i.e. bone) from another form of tissue (i.e. soft tissue). Once implanted, the barrier prosthesis would serve to protect a void or wound in one tissue (the bone) from encroachment by the adjoining (soft) tissue, which would otherwise grow unobstructed into the void, precluding the void from proper repair with the original type of (bone) tissue.

In EPA 0 274 898, Hinsch discloses a foam-like, resorbable, plastic material, incorporating textile reinforcing elements made from resorbable plastic embedded in an open-cell plastic matrix, the open-cell matrix formed by a vacuum, freeze drying process. The application disclosure includes tables demonstrating how the tensile strength of the implant increases upon addition of the textile reinforcing elements. This increased tensile strength results in an implant that is more resistant to pulling and tearing forces. One of the stated objectives of the invention is to have an open cell structure to permit the growing in of cells and blood vessels, yet still retain adequate tensile strength to serve as an implant. According to the disclosure, the pores must be of sufficient average size to allow the ingrowth of cells and blood vessels.

The aforementioned application EPA 0 274 898 (Hinsch), as well as U.S. Pat. No. 4,186,448 (Brekke), U.S. Pat. No. 6,031,148 (Hayes) and U.S. Pat. No. 5,855,608 (Brekke) disclose resorbable prostheses used to fill or cover tissue voids, relying on the formation of new bone and tissue within the implant. None of these disclosures anticipate the need of a prosthesis that conforms to a surgical site via collapse of pores and is utilized to anchor tissue fragments together.

The use of composites in prostheses has been used to improve both mechanical and biological properties. In PCT application WO 86/00533, for example, Leenslag discloses a composite of fiber material, which may or may not be biodegradable, incorporated in a porous matrix of a biodegradable organic polymer material. The material as described by Leenslag is suitable for repair or replacement of torn bony material, the term bony material as used therein referring to a damaged meniscus, not to a wound in a bone as contemplated by the subject invention. The design of the prosthesis is such that it requires rapid ingrowth of tissue and vessels as part of its function.

Bowman et al., in U.S. Patent Application Publication No. US 2002/0127265 A1, describes a biocompatible tissue repair stimulating implant or "scaffold" device. The application discloses an implant that facilitates cellular ingrowth, by the open cell foam structure of the polymer, as well as by the delivery of tissue growth stimulating compounds as biological agents within the device. The implant as described may incorporate at least one layer of a mesh or weave of fibers to lend mechanical support to the device, in order to enable the device to be handled in the operating room prior to and during implantation, to enable the implant to resist suture pull through, and to enable the foam device to withstand stresses placed upon it while implanted. This compound implant of foam and fiber reinforcement is implanted with the aim of encouraging tissue ingrowth into the implant, such that as the device is reabsorbed, tissue growth penetrates into the device.

Both the Leenslag patent and the Bowman application are for devices operating in a manner similar to the aforementioned devices disclosed by EPA 0 274 898, U.S. Pat. No. 4,186,448, U.S. Pat. No. 6,031,148 and U.S. Pat. No. 5,855,608, in that they function as a void filler or tissue replacement.

An implantable, bioresorbable membrane used to allow healing of a tissue defect site is disclosed by Yoon et al. in U.S. Pat. No. 5,948,020. As described therein, the membrane serves to isolate a tissue defect site from encroachment by adjoining tissue while allowing the wound to heal. The implant may also incorporate woven or knitted fabric made of bioresorbable fibers as a support embedded in a bioresorbable porous polymer matrix. To achieve sufficient malleability and dimensional stability, as well as to avoid prior art, the patent discloses an implant whose surfaces have been heated above the glass transition temperature to 150 C and forcing a plate with 20 protrusions/cm$^2$ into the already porous device (the embossing step).

Vyakarnum in U.S. Pat. No. 6,306,424 discloses an implant useful as a tissue scaffold, for repair or regeneration of tissue having architectural gradients (e.g. bone, cartilage, and skin), wherein the implant relies on gradients that mimic the histologic pattern of the tissues into which it is implanted.

There exists a need for an implantable, bioabsorbable prosthesis that is capable of being customized quickly, effectively and easily for the particular needs of each patient. The prosthesis should be capable of being fastened quickly and easily by a variety of fastening methods known in the art, including the use of staples, sutures, adhesives, nails, tacks, pins or clamps. The prosthesis must allow customization by responding to bending and compressive forces by smoothly bending and holding the desired shape, rather than cracking or breaking suddenly. The customization process should be simple, without requiring specialized tools or heating, thereby saving time and cost in the operation, as well as minimizing risk to the patient from prolonged exposure to infection and anesthesia. The prosthesis should allow the physician to make the customization in situ, while in the surgery suite, even while partially implanted. Furthermore, the absorbable prosthesis should be rigid enough to serve to isolate and protect the tissue from shifting. The prosthesis should be capable of being fully absorbed after the healing process has completed.

It is the intent of this invention to overcome these and other shortcomings of the prior art.

SUMMARY OF THE INVENTION

The present invention takes advantage of the porous structure of the prosthesis that allows deformation of the device without cracking or breaking of the structure. When bending pressure, for example, is applied, individual pores will collapse, allowing the smooth bending of the prosthesis in a radius, rather than a sudden collapse of the material as the prosthesis breaks. Similarly, if compressive force is applied, a portion of the pores may collapse, allowing the prosthesis to conform to the shape of the tissue it is pressed against, while maintaining the structural rigidity of the device.

While allowing the flexibility to be custom fit to the patient's tissue contours at room temperature in the operating field without special tools, the prosthesis retains enough structural rigidity and strength to lend structural support and protect a healing wound of a patient, e.g., to serve as a tissue or bone fixation device, a skull plate, or other prosthesis requiring structural rigidity. By altering the construction, such as varying the pore size and number or incorporating reinforcement materials, the physical characteristics of the prosthesis can be altered. In this fashion, a tissue fixation device, e.g., a bone plate, that is more compliant and having controlled structural stiffness due to incorporated pores may be manufactured. A tissue fixation device as described may be useful as a skull plate for example, where less flexing or stress is to be expected. Alternatively, by reducing the size and number of pores, a more rigid, and less compliant plate can be manufactured. Such a prosthesis would be more suitable for higher stress uses, including immobilizing bone fragments for broken ribs, pelvis, arms or legs as non-limiting examples.

The present invention is distinguishable from the prior art of porous tissue replacement devices, as the tissue replacement devices of the prior art serve to replace tissue temporarily, even so much as mimicking the tissue architecture replaced, and encourage the ingrowth of blood and tissue to allow new tissue growth to replace the bioeroding prosthesis. In contradistinction, the present invention serves to immobilize or hold two tissue areas together, functioning as a tissue joining device, and does not require the ingrowth of new tissue as the device bioerodes. The device of the present invention is capable of being bent or altered without requiring any extraneous steps, such as heating or embossing of the device.

These and other objects of this invention are achieved by providing a biodegradable prosthesis, the prosthesis being made of a porous polymer foam material or alternatively a composite of a porous polymer foam material and a reinforcing material. The prosthesis being capable of room temperature bending, yet retaining sufficient rigidity and strength to lend structural support and allow healing while in use. The unique use of pores within the current invention provides advantages over previously existing solid polymer and metal bone fixation plates, such as:

1) Flexibility over a wide range of temperatures, including room temperature.
2) Ability to be penetrated with fastening devices (e.g., pins, needles, tacks, screws, etc.) without preformed holes.
3) Ability to be sutured through its thickness and resist suture pull-through.
4) Pores allow for superior anchorage when using glues/ adhesives.
5) Ability to be cut and shaped using surgical scissors.
6) Ability to punch shapes out of large sheets of material.
7) Ability to deliver biologically active agents impregnated within the polymer of the prosthesis.
8) Ability to deliver biologically active agents impregnated within the pores of the prosthesis.
9) Ability to be impregnated with structural components.
10) Ability to be formed as a multi-phasic device.
11) Ability to be formed as a gradient device.
12) Mass of device can be modified by changes in porosity and/or addition of structural components.
13) Rigidity of device can be modified by changes in porosity and/or structural components.
14) Device can be bent or shaped without deformation of preexisting anchorage holes.

DESCRIPTION OF THE DRAWINGS

FIG. 2 (a) Cross-section view of the prosthesis showing regular, ordered pores; (b) cross-section view of the prosthesis having regular, ordered pores showing the prosthesis being bent, along with the resulting compression and subsequent collapse of pores on inside portion of curve; (c) cross-section of prosthesis having a porous layer and a solid or nearly solid layer; (d) cross-section view of the prosthesis having a porous layer and a solid or nearly solid layer, showing the prosthesis as it is being bent, along with the resulting compression and subsequent collapse of pores on inside portion of curve, and smooth bend of solid or nearly solid layer; (e) cross-section view of the prosthesis having a porous layer, a solid or nearly solid layer, and a second porous layer; (f) cross-section of prosthesis having a porous layer, a solid or nearly solid layer, and a second porous layer, showing the prosthesis experiencing multiple bending forces, along with the resulting compression of pores on inside portions of the curves, and smooth bending of solid or nearly solid layer.

FIG. 3 (a) Cross-section view of the prosthesis showing porous zones, and (b) cross-section of prosthesis under compressive force, showing collapse of a portion of a zone of pores to conform to shape pressed against, and (c) cross-section of prosthesis being bent, showing compression and subsequent collapse of pores on inside portion of curve.

FIG. 4 Perspective and partial cutaway view of suture and other fastening devices penetrating through the prosthesis.

FIG. 7 (Prior Art) Cross-sectional views of (a) a solid polymer bone plate as known in the prior art, and (b) a solid polymer bone plate, known in the prior art, as a bending force is applied at a temperature less than that of the glass transition temperature for the polymer.

DETAILED DESCRIPTION OF PREFERRED EMBODIMENTS

Figure 1B:
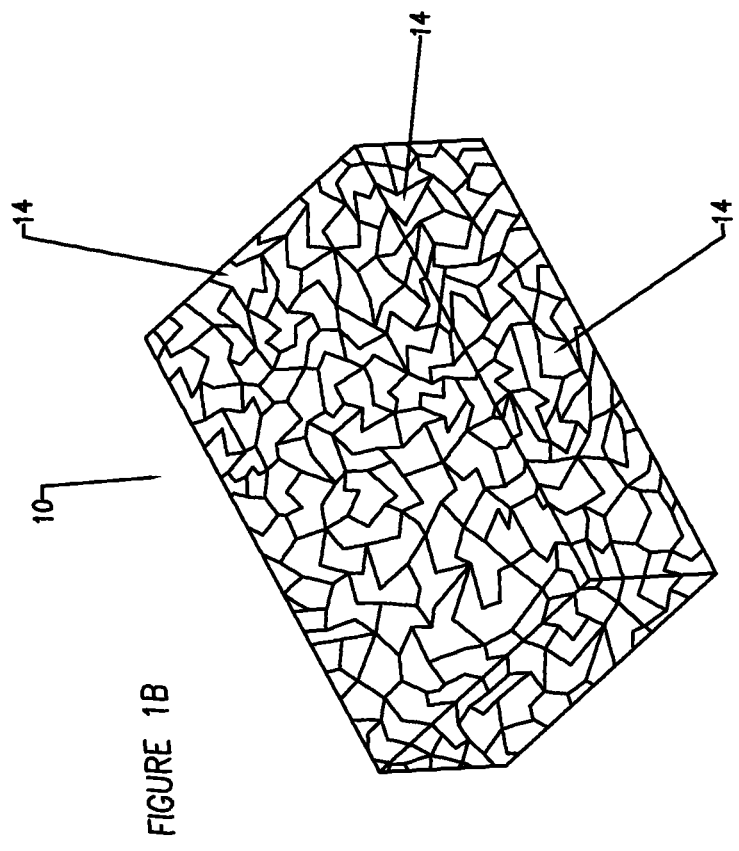
FIG. 1 (a) Perspective view of prosthetic material shaped as a rectangular bone plate having regular, ordered pores; (b) perspective view of prosthetic material shaped as a rectangular bone plate having irregular, random pores.

The object of the invention is an implantable prosthesis, constructed of a porous, resorbable, polymer material. The material comprising the prosthesis or device (as used herein, the terms prosthesis and device are used interchangeably) is a resorbable polymer that is biocompatible with the systems of a living being. The construction of the prosthesis is such that it is to be capable of easily being shaped. The shaping may occur in a variety of manners, such as by bending or compressing to conform to a desired shape without requiring any source of heating or special tools, and upon removal of the bending or shaping force, the prosthesis will remain in the exact shape, or nearly so; thus enabling the prosthesis to fit the unique contours of each patient. Despite being easily manipulated by hand, the prosthesis remains rigid and strong enough to lend structural support, and allows protection to the wound of a living being while the healing process occurs. The device has several advantages over metal prostheses, including the resorbable nature of the prosthesis, which obviates the need for a second invasive surgery to remove the device, also the ability to be shaped without the need for special tools and/or equipment.

The prosthesis may be sterilized by any low temperature methods known in the art (e.g. exposure to ethylene oxide, hydrogen peroxide gas plasma, e-beam irradiation or gamma irradiation). The sterilization minimizes the opportunity of infection to occur as a result of the implant.

In the preferred embodiment of the invention, the porous prosthesis is manufactured from a resorbable material. The resorption rates of resorbable polymers can be controlled by varying the polymer material, molecular weight, additives, processing, and sterilization. Resorption rates can be adjusted to be shorter for applications that require mechanical strength for only a short period of time or longer for applications that require mechanical strength to be present for a longer duration. Examples of resorbable polymers that can be used to form the prosthesis are shown in following Table 1. These materials are only representative of the materials and combinations of materials, which can be used as prosthetic material.

TABLE 1

Examples Bioresorbable Polymers for Construction of the Device of the Current Invention:

Alginate
Aliphatic polyesters
Cellulose
Chitin
Chitosan
Collagen
    Types 1 to 20
    Native fibrous
    Soluble
    Reconstituted fibrous
    Recombinant derived
Copolymers of glycolide
Copolymers of lactide
Elastin
Fibrin
Glycolide/l-lactide copolymers (PGA/PLLA)
Glycolide/trimethylene carbonate copolymers (PGA/TMC)
Glycosaminoglycans
Lactide/tetramethylglycolide copolymers
Lactide/trimethylene carbonate copolymers
Lactide/$\epsilon$-caprolactone copolymers
Lactide/$\sigma$-valerolactone copolymers
L-lactide/dl-lactide copolymers
Methyl methacrylate-N-vinyl pyrrolidone copolymers
Modified proteins
Nylon-2
PHBA/$\gamma$-hydroxyvalerate copolymers (PHBA/HVA)
PLA/polyethylene oxide copolymers
PLA-polyethylene oxide (PELA)
Poly (amino acids)
Poly (trimethylene carbonates)

TABLE 1-continued

Examples Bioresorbable Polymers for Construction of the Device of the Current Invention:

Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-$\beta$-hydroxypropionate (PHPA)
Poly-$\beta$-hydroxybutyrate (PBA)
Poly-$\sigma$-valerolactone
Poly-$\beta$-alkanoic acids
Poly-$\beta$-malic acid (PMLA)
Poly-$\epsilon$-caprolactone (PCL)
Pseudo-Poly(Amino Acids)
Starch
Trimethylene carbonate (TMC)
Tyrosine based polymers Two exemplary processes which may be used for making the present resorbable porous polymeric fixation plate are the "plasticized melt flow" or PMF, and "phase separation polymer concentration" or PSPC.

In the PMF process, the nucleating agent, if any, can be mixed into a gas-permeated plasticized polymer. The gas (e.g. air, oxygen, carbon dioxide, nitrogen, argon, or any inert gas, including combinations thereof) trapped within the polymer begins to expand as the pressure external to the polymer is reduced. As the gas expands it attempts to create uniformly dispersed homogeneous spherical pores. When a nucleating agent is present, the growth of the pores is disrupted as the walls defining the pores thin to the point that the nucleating agent begins to protrude. In this case, the nucleating agent may act as a "modeling agent". As the gas continues to expand the modeling agent particles begin to interfere with each other and/or the expanding pore walls, and force the pore to take on an irregular shape.

In the PSPC process, the modeling agent is dispersed within a polymer solvent solution. The temperature of the mixture is lowered until crystals form within the solution. As the crystals grow they force the polymer into a smaller and smaller area similar to the expanding gas in the PMF process. The growth of the crystals is disrupted as they come in contact with the modeling agent. As the crystals continue to grow they press the modeling agent particles in contact with each other and are thus forced to grow around the particles in an irregular fashion. After solidification vacuum or leaching, a chilled non-solvent removes the solvent crystals.

By varying the ratio of polymer to modeling agent in the PMF and PSPC processes, the porosity, pore surface texture and geometry of the matrix may be controlled; wherein the matrix is polymer, molding agent and porosity combined.

Low polymer constituent concentrations combined with longer processing times allows the growth of large pores, thereby affecting mechanical and physical properties. The rate at which the pores grow (via gas expansion or crystal growth, as appropriate) can determine where in the polymer mass the modeling agent is located. Slow growth of pores allows the modeling agent to migrate within the thinning polymer walls and remain covered or encapsulated. Rapid expansion of the pores does not allow sufficient time for the modeling agent to migrate within the walls resulting in partial exposures of the modeling agent. The modeling agent may also control physical and biologic properties. For example, the incorporation of high modulus strengthening components (e.g., polymers, ceramics or metallics) in various forms (e.g., particulate, fiber, whisker, etc.) as the modeling agent will affect the strength and toughness of the resulting structure.

The modeling agent does not just affect mechanical properties, but rather can serve multiple purposes, which may include but are not limited to:
1. creating a textured surface on the internal surfaces defining the pores;
2. creating a microporous conduit system between pores;
3. reaction-extraction of endogenous growth factors;
4. carrying and/or delivering drugs, biologically active or therapeutic agents;
5. function as a drug, biologically active or therapeutic agent;
6. modifying mechanical properties (e.g. strength, flexibility, etc);
7. function as an in-vivo leachate to increase the overall porosity.

The irregular pore surfaces formed by the modeling agent serves multiple purposes, which may include but are not limited to:
1. increased surface area provides greater numbers of anchorage points for cell attachment;
2. increased surface area permits modification to the leaching rate of drugs or other therapeutics;
3. textured surfaces increase quantity of material that can be coated on the interior pore surfaces;
4. irregular surfaces increase the resistance to flow through the implant.
5. engineered surfaces can affect how cells attach, thereby modifying the resulting tissue that is generated.
6. engineered or roughened surfaces can alter the overall pore geometry, which can affect stresses on differentiating cells, thereby dictating cell differentiation modalities.

Figure 1A:
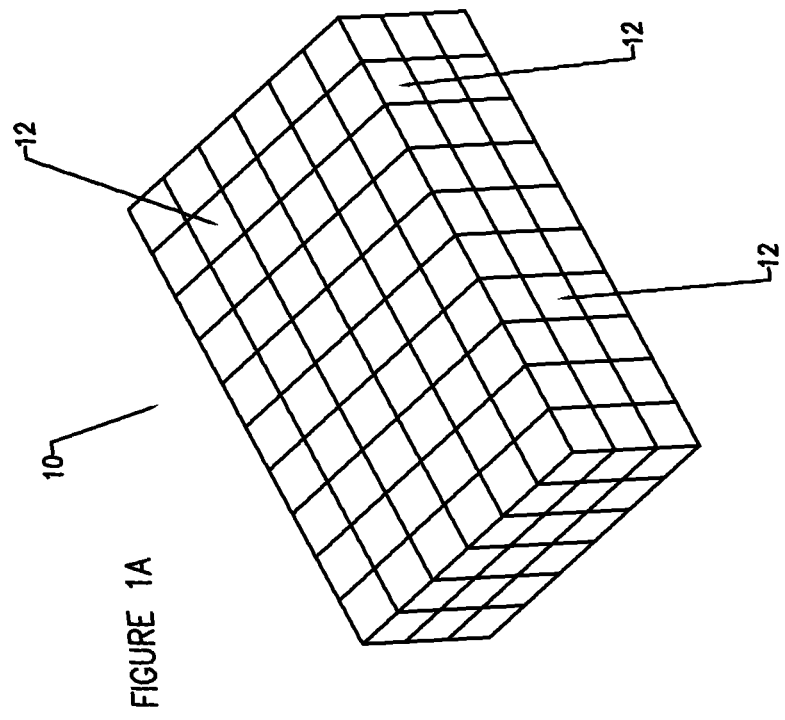

Referring now to the drawings, wherein like reference characters refer to like parts, one contemplated embodiment of the invention is shown in FIG. 1a. In this embodiment of a polymer tissue fixation device, the regular ordered pores 12 comprising the porous material of the prosthesis 10 is produced in the approximate shape required for use as a bone plate implant for a patient. Similarly, as shown in FIG. 1b, the porous material of the device 10 is composed of random, irregular pores 14. In either of these embodiments of the invention, where the device 10 is to be utilized to stabilize a fissure created in the parietal bone during the course of cranial surgery, a flat disk or rectangle shape might suffice, as shown. The height of the disk would be such that while fastened to the skull by any suitable means known in the art (e.g., adhesives, clamps, medical staples, nails, pins, tacks, screws, sutures, or wires), the implant would not protrude markedly from the skull and would allow replacement of the scalp to cover the implant. Similarly, the same implantable device might be used to cover a hole drilled or a void cut in the parietal bone. Such an implant would not be subjected to high physical stresses, and can be manufactured in an appropriate manner to create a more compliant plate, such that it is capable of complying with the curves of the skull surfaces.

The surgeon, prior to implantation, may customize the length, width, and shape of the implantable device. These alterations may include bending a specific portion of the device, cutting to the desired size or shape, or punching holes. Due to the porous nature of the implant, the alterations may be performed quickly by hand, or alternatively facilitated through the use of simple hand tools, for example a scalpel, scissors, a needle or an awl. In contrast, prior art metal bone plates are relatively difficult to bend to a desired shape and are not capable of being cut or have holes punched through directly before implanting in the patient. Similarly for the prior art non-porous polymer bone plates that require heating to the glass transition temperature in order to be bent without cracking or breaking, and are also not capable of being cut or having holes punched through just before use, as sharp edges, cracks or distortion of the implant would occur. The porous structure of the invention allows it to remain flexible over a wide range of temperatures, ranging from below freezing and up to the melting point of the specific polymer or combination of polymers. This low temperature flexibility allows the device to be simply and quickly bent or cut, contemporaneously with the ongoing procedure, therefore allowing the procedure to be completed in less time, and reducing the risk of harm to the patient. The physical characteristics of the subject invention are such that the surgeon has great flexibility in the customization process, the placement of holes, modifications of shape and various bends can easily be accomplished in manners not previously possible with prior art solid bone plates, whether metal or polymer. Additionally, should the surgeon choose, the porous polymer device could be heated above the glass transition temperature and preformed with greater ease than solid polymer devices due to the lower mass of the porous prosthesis, as compared to a solid prosthesis currently known in the art.

Referring again to FIG. 1a, a larger plate of the prosthetic material can be made, from which one or many different prosthetic devices 10 can easily be cut, and in this manner, a single piece may be capable of being shaped into several copies of the device 10, all which may then be altered further, if necessary, and implanted into a living being. This allows the surgeon great flexibility in deciding what size bone plate would be required, and the general shape required. Furthermore, due to the ease with which the plate material may be bent, and formed, the surgeon is able to achieve a custom fit for each patient very quickly, and with little time spent forming the prosthesis to fit.

Referring to the prior art depicted by FIGS. 7a and 7b, the effects of bending forces 80 (shown in orientation here by arrows) upon a solid, polymer bone fixation plate 75, as known in the prior art, is depicted in cross section. While at room temperature, and below the glass transition temperature of the polymer, bending forces 80 may be applied to the solid, polymer bone plate 75, however, due to the physical characteristic of the solid implant, the solid, polymer implant may flex, but will not readily conform to a different shape. Rather, as shown in FIGS. 7a and 7b, the plate 75 will either crack 77 or break 79. Contrast this now, with the porous material of the present invention, as depicted in FIGS. 2a and 2b, wherein the polymer device 10 is capable of being bent without requiring heating. A cross-sectional depiction of one possible embodiment of the invention is depicted in FIG. 2a, wherein device 10 is shown having regular ordered pores 12. FIG. 2b depicts the device 10 as it is being bent, wherein the bending force 80 is applied (shown in orientation here by arrows), causing the deformation and collapse of pores in the region along the inside of the bend 22. As discussed in further detail to follow, pores in the region on the outside of the bend 24 may also undergo a shape or size change, although it may be a more subtle change compared to those on the inside of the bend. The collapsing of the pores along the inside of the bend 22 serves to distribute the bending force 80 applied over an area comprising a radius, thereby ensuring that the prosthetic device 10 bends smoothly, forming a radius curve 26, rather than cracking or breaking, as would a solid piece of material (the prior art depicted in FIGS. 7a and 7b) with similar rigidity and without the porous construction 12 of the invention. Furthermore, after the bending forces 80 are released, the collapsed pores along the inside region of the bend 22 will not spring back to their original shape 12, rather they will remain substantially in the deformed and collapsed state, thereby ensuring that the smooth bend forming a radius curve 26 in the prosthesis 10 remains after the bending forces 80 are removed. Though not shown, a similar device constructed of random, irregular pores (as shown in FIG. 1b) would behave similarly under the application of bending forces, forming a smooth radius curve by the collapse of pores along the inside region of the curve.

Figure 8A:
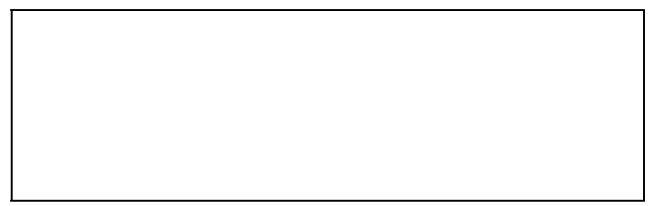
FIG. 8 Instructional depictions of a beam in (a) an unbent condition, and (b) a bent condition.
Figure 8B:
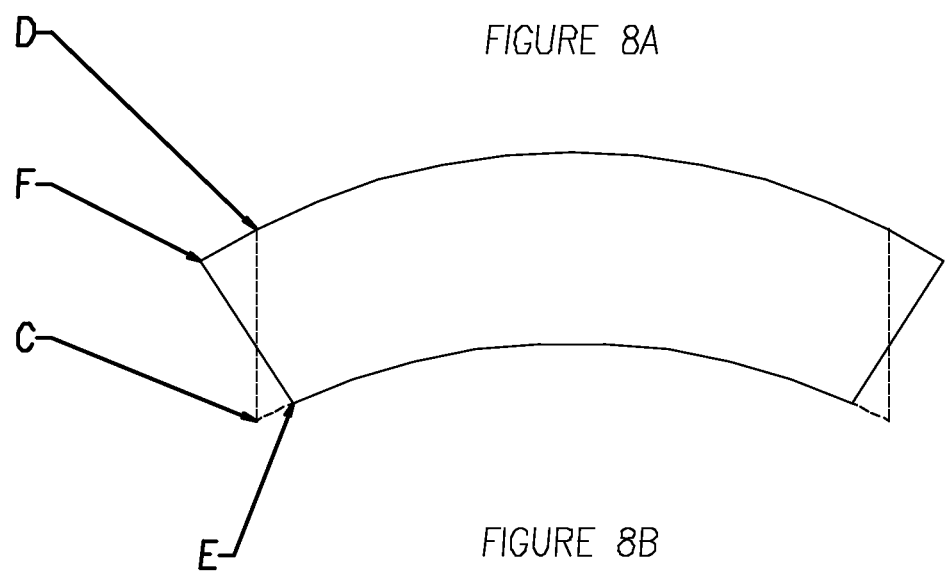

The collapsing of a porous layer along the inside of a bend permitting the bending of a solid or nearly solid layer into radii previously unachievable without cracking or breaking can be seen by referring to FIGS. 8a and 8b. These figures depict a beam being bent in an arc. In the unbent condition (FIG. 8a), the upper and lower surfaces have the same length, but in the bent condition (FIG. 8b), one can see that both surfaces are strained. In particular, the upper surface is distended or stretched, and the lower surface is shortened or compressed. This arises because the upper and lower surfaces are connected to one another, and they try to maintain their continuity after bending. Thus, the upper surface is in a state of tensile stress, and the lower surface is in a state of compressive stress. Moreover, there is a region between the upper and lower surfaces that does not change in length, and this zone is in a neutral stress state, being neither compressed nor in tension. One can also see from the bent beam of FIG. 8b that the sharper the bend, the smaller are the radii at the inner and outer surfaces, and the greater the amount of strain (i.e., fractional change of length) there is of these surfaces.

Consider now that the beam is porous, or at least porous at its upper and lower surfaces. The collapsing of pores on and near the lower surface is a response to the compressive stress, and an accommodation of this stress since the material reacts to an externally applied stress in such a way as to minimize internal stress. In other words, the collapsing of pores at the lower surface reduces the amount of compressive stress. Similarly, the pores on and near the upper surface are under a tensile stress due to the bending, and can respond to this stress by becoming more elongated in the tensile direction. This elongation is often accompanied by a shortening of the pore in a direction perpendicular to the tensile direction, i.e., a flattening of the pore, so this, too, can be thought of as a collapse of the pore. Because the compressive and tensile stresses must be in balance, the relaxation of stress at one surface, e.g., due to collapsing or pores, also causes a relaxation of stress at the opposite surface. Accordingly, the collapsing of pores permits amounts of bending that would otherwise cause cracking or breaking of the solid polymer in beams not having such a porous layer.

Another way of looking at the stress and strain states in the bent beam is as follows. The bent beam would like to keep the upper and lower surfaces the same length, so the left edge of the bent beam would be represented by line c-d. But this it cannot do, since the upper surface is firmly connected to the bottom surface, so the left edge ends up being represented by line e-f. Thus, the bottom surface is shortened as compressed pores collapse, and the upper surface is lengthened as pores in tension also collapse in a direction normal to the tension. The collapsing pores serve to relieve the compressive and tensile stresses, and thus relaxing the overall stress state of the material. This relaxation allows the material to deform with lower stress, when compared with non-porous materials.

Similarly, supplying a porous layer or section at or near an outer surface of an otherwise non-porous structure will allow stress relaxation through the collapsing (or elongation) of the pores. This relaxation will allow deformation at lower stresses, thereby allowing more strain to be experienced before the critical breaking stress is reached.

FIGS. 2c and 2d depict a cross-sectional view of another possible embodiment of the device 10, comprising a porous layer 19 of ordered pores 12 and a layer of solid or nearly solid material 16. The transition from porous material 12 to a solid material 16 may be an abrupt transition 28 as depicted, or alternatively the transition may be a gradual transition that occurs as the size and population density of the pores decreases gradually in construction (not shown). Behaving similarly to the depictions of FIGS. 2a and 2b, the dual layer prosthesis of FIGS. 2c and 2d is capable of being smoothly bent, by forming a radius curve 26 when bending forces 80 are applied. In the depiction of FIG. 2d, the pores 12 comprising the porous layer 19 along the inside of the bend 22 will collapse, and allow the formation of a radius in the solid or nearly solid layer 16 of material along the outside of the bend 24; resulting in a smooth bend rather than cracking or breaking as would the prior art of FIGS. 7a and 7b. Though not shown, a device constructed from a dual layer device composed of a layer of random, irregular pores and a solid or nearly solid layer would exhibit bending behavior similar to that shown by FIGS. 2c and 2d.

As a non-limiting example, the dual layer device 10 of FIG. 2c may comprise a solid or nearly solid layer 16 of synthetic polymer (e.g., PGA, PLA, etc.), and the regular, ordered porous layer 19 may be formed of a porous matrix of non-synthetic material (e.g., collagen, alginate, chitosan, etc.) Due to the nature of the materials utilized for this particular example, the porous layer 19 composed of non-synthetic material, will, while dry, afford structural support to facilitate the bending of the solid layer 16, by selectively collapsing a portion of the pores 12. However, when wetted (e.g., after implantation, or exposure to a liquid or solvent), the layer of regular, ordered porous material 19 comprised of non-synthetic material loses its rigidity and becomes soft and compliant, or alternatively may quickly be dissolved entirely, leaving only the synthetic solid or nearly solid layer 16 of the device 10, as the non-synthetic polymers are soluble in tissue fluids, or lose structural rigidity when wetted. The porous material layer may be composed of irregular random pores, and exhibit a similar behavior, though this is not shown.

Due to the construction of the dual layer device of FIGS. 2c and 2d, the smooth bending may occur causing the regular, ordered porous layer 19 to form the inside of the curve 22. As the bending forces 80 are applied, they cause the collapse of the regular, ordered pores 12, with the collapsed pores distributing the bending forces 80 over a radius, thus permitting the smooth bending of the solid or nearly solid layer 16.

As shown in FIGS. 2e and 2f, the multi-layer construction herein has more than two layers. In this embodiment, there is shown a solid or nearly solid layer 16, sandwiched between regular ordered porous layers above 20 and below 21. Though it is recognized, but not shown, that the irregular, random pores would behave similarly. In this embodiment, bending forces 80 may be applied in either orientation, and as the pores 12 are able to collapse and distribute the bending forces in either direction, more elaborate multi-directional bends are possible, without breaking the solid or nearly solid layer 16 as the bending forces 80 would form radius curves 26, and with multiple curves may allow 's' bends or other types of bends.

A cross-sectional depiction of an alternate embodiment of the invention is depicted in FIG. 3a. The prosthesis 10 of FIG. 3a features a laminar construction, which comprises a series of layers 31,32,33 of varying pore sizes and pore densities. Though the depiction here is of regular ordered pores 12, this is for ease of illustration, and may suitably be irregular, random pores. It is contemplated that the prosthesis 10 be made entirely of one resorbable material, or alternatively, with each of the layers of the laminar construction 31, 32, 33 comprising the same or a different resorbable material. Furthermore, the prosthesis 10 of this embodiment or any other of these embodiments may be fabricated by adding at least one reinforcing material to the prosthesis (to be discussed later).

As shown in FIG. 3c, the varying pore sizes of the layers 31, 32, 33 would offer varying resistance to collapse, with the larger pores of layer 31, being more easily collapsed than the smaller pores of the intermediate layer 32, which in turn would be more easily collapsed than the even smaller pores of the smallest pore layer 33. It is recognized that in order for the existence of multi-layer construction, at least two layers are needed. For ease of illustration, three distinct layers are depicted by FIGS. 3a, b, and c, but it is recognized that there may be more or less layers. It is also recognized that the interface or transition between the layers may be gradual or abrupt; for ease of illustration, abrupt interfaces between the distinct layers are depicted. It is also recognized that the distinction of layers may be based upon some other characteristic than pore size, such as pore density, material of construction, or some other identifiable quality, for ease of illustration, the distinction is made by pore size and pore density.

This multi-layer construction depicted by FIG. 3c would allow bending forces 80 to be applied (shown in orientation here by the large black arrows) upon the device 10, with the resulting smooth bend in a radius curve 26 demonstrated by FIG. 3c. As a result of the laminar construction, incorporating differing layers having varying resistance to collapsing of the pores, a more suitable bone plate may be constructed, relative to a non-porous bone plate; yet the laminar porous construction will retain the ability to be smoothly bent to facilitate customization of the implant. This may be accomplished, for example, by reducing the pore sizes in the layer 33 along the outside of the bend 24, resulting in greater strength in that layer 33, and at the same time, increasing the pore sizes in the layer 31 along the inside of the bend 22, where additional flexibility is gained by the more easily collapsed pores of the larger pore layer 31. In this manner, the prosthesis 10 is able to bend smoothly, forming a radius curve 26, rather than breaking as it would if the same bending force 80 (referring to the prior art of FIGS. 7a and 7b) was applied and absorbed by only a small area, such as along a narrow crease in the fold or bend of the solid plate 75.

Furthermore, when bending forces 80 are removed, the smooth bend of the radius curve 26 in the multi-layer device shown by FIG. 3c will remain, as the irreversibly collapsed pores along the inside region of the curve 22 will not return to their original shape.

It is recognized that a great number of layers may be constructed into the device, comprising various combinations distinguishable by their number, structure, or other distinguishable characteristics; such as the structural properties of the device may be altered by creating different combinations of layers, pore sizes, construction materials or other structural qualities.

A prosthesis constructed as shown in FIG. 3a would be able to conform to the shape of an uneven surface, as depicted in FIG. 3b. This may be accomplished by applying compressive force 81 (shown in orientation here by arrows) upon the device 10, compressing the device evenly against an exposed uneven surface 36, with resistance 82 (shown in orientation here by arrow) offered by the uneven surface 36 against the device 10. As a result of the compressive force 81 and resistance 82, the initial resistance from the protruding areas 38 would selectively deform and collapse the larger and more easily collapsed layer of pores 31, and to a lesser extent the intermediate pores of layer 32, the affected pores located proximally to the protrusion area 38, leaving the layers with smaller pores 33 intact. Furthermore, the recessed areas 39 of the uneven surface 36 would not deform or collapse any of the pores in the layers 31, 32, 33. As a result of the compressive force 81 and the resistance 82, affecting the pore structure of the device 10, the prosthesis surface may be altered to take on the inverse shape of the exposed surface 36, and therefore complies with the uneven surface 36. Upon removal of the compressive force 81, the device 10 will not spring back elastically to the original shape due to the fact that a portion of the pores 12 had irreversibly collapsed.

Referring to FIG. 4, wherein a prosthesis 10 having random, irregular pores 14 is depicted, the prosthesis 10 with random pores 14 is capable of being used with fastening systems known in the art. Though not shown, an alternate embodiment of the device having regular ordered pores would similarly be capable of being used with fastening systems known in the art. These fastening systems may include adhesives (not shown), medical staples 42, pins (not shown), nails 44, tacks (not shown), screws 46, or clamps (not shown), among other suitable fastening devices.

In one embodiment, the prosthetic device 10 may be manufactured incorporating a hole 40, or alternatively a plurality of holes (not shown), extending at least partially through the prosthesis 10, which could accommodate the use of a suitable fastening method, such as e.g.; screws 46 or nails 44, to fasten the implantable device 10 through a pre-existing hole 40. Depending on the intended use of the prosthesis 10, the hole 40 may be created during the manufacturing process.

Preferably, the surgeon would be able to further customize the implantable device 10 by creating any number of needed holes 40 for the procedure. This may be accomplished by use of a hole-punch device, alternatively by a scalpel, scissors, the use of a cutting blade, or by any means suitable to penetrate into and through the prosthesis. The tool will displace and deform the porous structure it comes in contact with, such as in separating the material in making a hole 40, leaving the pores more distant from the tool intact. In this manner, a hole 40 may be made in the prosthesis 10, without large-scale tearing or splitting of the prosthesis, as only the pores closest to the tool would be disturbed, and thereby limit the effect upon pores away from the tool. When used in this manner, the physician retains the flexibility to locate the fastening points where, in the physician's judgment, they are most appropriate, without requiring pre-manufactured fastening points in the prosthesis 10.

Most preferably, the prosthetic device 10 may be put in place, and fastened without the use of pre-manufactured holes in the prosthesis. This allows the physician to simply fasten the prosthesis 10 by any suitable means known in the art, such as by forcing a screw 46, nail 44 or staple 42 through the implant, wherein the porous structure 14 of the device 10 limits the amount of large scale tearing that may occur, as only the pores closest to the tool will be affected, leaving the rest of the device intact. When used in this manner, the physician has flexibility to locate the fastening devices in situ, without needing to approximate where the location needs to be created. As a result, there would not be a need to fit the prosthesis 10 to the appropriate shape, and then make the holes away from the patient; rather the prosthesis 10 could be fitted to shape, and while the prosthesis 10 is in place, simply fastened into location by any suitable fastening means known in the art, without requiring the existence of a pre-existing hole 40. As an alternative to the use of rigid fastening systems, such as screws 46 or nails 44 to fasten the prosthesis 10, the porous structure of the device 10 with irregular pores 14, and also having regular ordered pores (not shown) is capable of being sutured 48 as shown in FIG. 4. The suture 48 may be non-resorbable, or preferably be of a resorbable nature, so that it may dissolve over time, along with the prosthesis 10. The porous structure is compatible with the use of a suture 48 as the porous structure of the device 10 will accommodate a needle by the pores separating as the needle penetrates, whether through the entire thickness of the prosthesis, or merely through a portion of the thickness of the prosthesis. The porous structure of the device 10 is able to resist suture pull-through, as the pulling force exerted by the suture may be distributed over a large number of pores. For this reason, the thread of the suture 48 will not easily rip through the structure and pull out. By use of a suture 48, the prosthetic device 10 may be attached to soft tissue, without requiring a pre-manufactured hole 40 for suturing, or attachment of sutures before use.

Still another alternative fastening method relies on the use of adhesives to attach the prosthesis in place (not shown). While using adhesives, a portion of the pores along the surface will be in contact with, and may absorb a portion of a liquid adhesive. As the adhesive sets, the prosthesis will be attached to the tissue. Suitable adhesives include fibrin, polymer, or cyanoacrylate glue, as well as others known to those skilled in the art. Such adhesives may be capable of penetrating into the porous material of the implantable device 10, with the effect of multiplying the bonded surface area, thereby resulting in a bond stronger than would be available if merely the exposed outer surface of the implant was coated by the adhesive.

Figure 5:
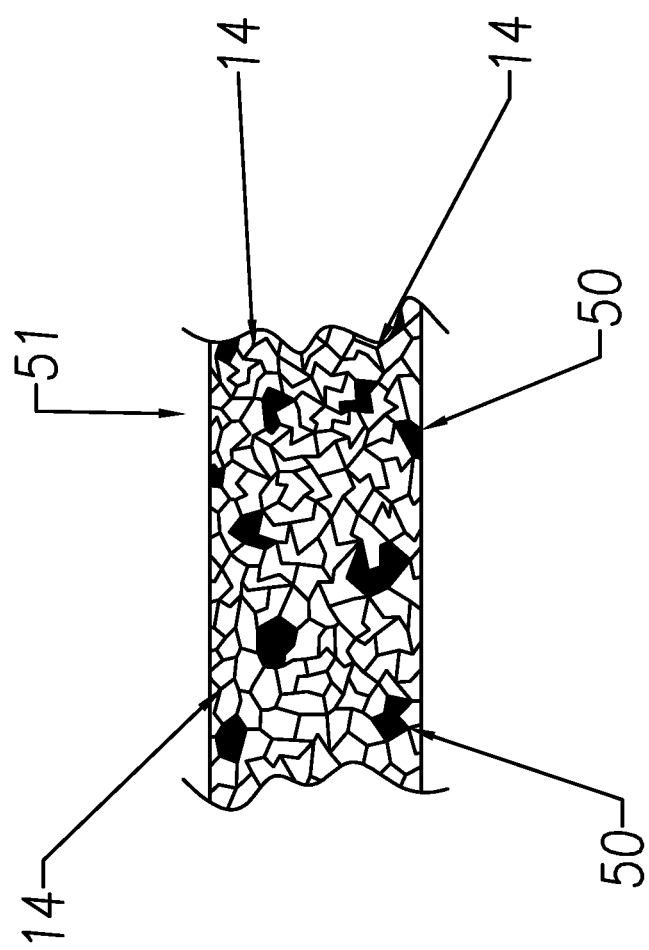
FIG. 5 Cross-section view of the prosthesis having a random, irregular, porous structure and also having particulate material or biologically active agents.

As shown in FIG. 5, a cross-sectional depiction of the device as a composite 51, comprising the device as previously described, as well as featuring further additional materials 50. The depiction of FIG. 5 is of a composite device 51 having random, irregular pore structure 14; however, it is recognized that the composite device 51 may have regular ordered pore structure as well, and further containing additional material 50. In one embodiment, the additional materials 50 may be high modulus strengthening components (e.g., polymers, ceramics or metallics), where the high modulus material will affect the physical characteristics of the composite prosthesis 51, such as increasing the rigidity, strength, and toughness of the resulting structure. The strengthening agent may be in various forms (e.g., particulate, fiber, whisker, mesh, weave, knit, yarn, etc.). The additional material may be uniformly distributed throughout the entire composite prosthesis 51, or alternatively selectively incorporated to achieve a desired effect.

The same additional material 50 incorporated to achieve a desired effect upon the physical properties of the composite implantable device 51 may also affect its biologic properties. As an example, hydroxyapatite would not only improve the strength of the implant, but also be capable of, for example, extracting endogenous growth factors from the host tissue bed while functioning as a microporous conduit facilitating movement of interstitial fluid throughout the isolated porosities of the device. In another embodiment, the additional materials 50 may alter the resorption qualities of the resorbable porous material. Other non-limiting examples of suitable materials that may be added to the prosthesis are listed in Table 2.

TABLE 2

Examples of Materials Incorporated into the Composite Device in Accordance with the Present Invention Alginate
Bone allograft or autograft
Bone Chips
Calcium
Calcium Phosphate
Calcium Sulfate
Ceramics
Chitosan
Cyanoacrylate
Collagen
Dacron
Demineralized bone
Elastin
Fibrin
Gelatin
Glass (e.g.- Bio-Glass)
Gold
Glycosaminoglycans
Hydrogels
Hydroxyapatite
Hydroxyethyl methacrylate
Hyaluronic Acid
Liposomes
Microspheres
Natural Polymers
Nitinol
Oxidized regenerated cellulose
Phosphate glasses
Polyethylene glycol
Polyester
Polysaccharides
Polyvinyl alcohol
Radiopacifiers
Salts
Silicone
Silk
Steel (e.g. Stainless Steel)
Synthetic polymers
Thrombin
Titanium
Tricalcium phosphate The additional material 50 can serve multiple purposes, which may include, but are not limited to:
1. creating a textured surface on the internal surfaces defining the pores;
2. creating a microporous conduit system between pores;
3. reacting-extracting of endogenous growth factors;
4. carrying and/or delivering drugs, biologically active or therapeutic agents;
5. functioning as a drug, biologically active or therapeutic agent;
6. modifying mechanical properties (e.g. strength, flexibility, suture retention, etc.);
7. functioning as an in-vivo leachate to increase the overall porosity.

The textured surface created by the additional material 50 additionally serves multiple purposes that may include but are not limited to:
1. increased surface area permits modification to the leaching rate of drugs or other therapeutics;

2. textured surfaces increase quantity of material that can be coated on the interior pore surfaces;
3. irregular surfaces increase the resistance to flow through the implant.

Additional materials 50 may also be used at the time of manufacture to control the process output (e.g. plasticizers, surfactants, dyes, etc.) For example, processing the polymer with stearic agents will cause the thinning of matrix between the pores, which is most easily penetrable, or rapidly resorbing, following implantation. This will result in a composite device 51 with high strength, and interconnected pores.

The additional materials 50 may lend some other desired property to the composite prosthesis 51, such as the capability of delivering biologically active agents, or of being radio-opaque, in order to allow imaging by x-ray or MRI techniques while the prosthesis is implanted or being implanted in the living being. The additional material 50 would be capable of being resorbed in the body, either at the same rate of absorption as the polymer or at a faster or slower rate of resorption. Should the prosthesis further contain biologically active agents, they may be delivered slowly as the surrounding porous material is resorbed. Alternatively, if the biologically active agents comprising the additional material 50 are easily dissolved, tissue fluids may be capable of leaching out the agents as the tissue fluids permeate the porous structure of the composite prosthesis 51. Examples of biologically active agents that may serve as the additional material 50 of the composite prosthesis 51 are listed in Table 3.

The additional material 50 may be in the form of microspheres. Microspheres can be made of a variety of materials such as polymers, silicone and metals. Biodegradable polymers are ideal for use in creating microspheres for use in these embodiments (e.g., see those listed in Table 1). The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. It is well known that there can be different mechanisms involved in implant degradation like hydrolysis, enzyme-mediated degradation and bulk or surface erosion. These mechanisms can alone or combined influence the host response by determining the amount and character of the degradation product that is released from the implant. In the extracellular fluids of the living tissue, the accessibility of water to the hydrolysable chemical bonds makes hydrophilic polymers (i.e. polymers that take up significant amounts of water) susceptible to hydrolytic cleavage or bulk erosion.

Several variables can influence the mechanism and kinetics of polymer degradation. Material properties like crystallinity, molecular weight, additives, polymer surface morphology, and environmental conditions. As such, to the extent that each of these characteristics can be adjusted or modified, the performance of this invention can be altered. These microspheres, serving as the additional material 50 in the composite device 51, may further contain and/or deliver biologically active agents from Table 3.

TABLE 3

Examples with Some Types of Biological, Pharmaceutical, and other Therapies that can be Delivered via the Composite Device in Accordance with the Present Invention Adenovirus with or without genetic material
Angiogenic agents
Angiotensin Converting Enzyme Inhibitors (ACE inhibitors)

TABLE 3-continued

Examples with Some Types of Biological, Pharmaceutical, and other Therapies that can be Delivered via the Composite Device in Accordance with the Present Invention Angiotensin II antagonists
Anti-angiogenic agents
Antiarrhythmics
    Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
Anti-proliferation agents
Anti-rejection agents
    Rapamycin
Anti-restenosis agents
Antisense
Anti-thrombogenic agents
    Argatroban
    Hirudin
GP IIb/IIIa inhibitors
Anti-virus drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    Indian hedgehog (Inh)
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
    Stem cells
    Bone Marrow
    Blood cells
    Fat Cells
    Muscle Cells
    Umbilical cord cells
Chemotherapeutic agents
    Ceramide
    Taxol
    Cisplatin
    Paclitaxel
Cholesterol reducers
Chondroitin
Clopidegrel (e.g., plavix)
Collagen Inhibitors
Colony stimulating factors
Coumadin
Cytokines prostaglandins
Dentin
Etretinate TABLE 3-continued Examples with Some Types of Biological, Pharmaceutical, and other Therapies that can be Delivered via the Composite Device in Accordance with the Present Invention Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Autologous Growth Factors
    B-cell Activating Factor (BAFF)
    Bovine derived cytokines
    Cartilage Derived Growth Factor (CDGF)
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Tissue derived cytokines
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukins
    Interlukin-8 (IL-8)
Lipid lowering agents
Lipo-proteins
Low-molecular weight heparin
Lymphocites
Lysine
MAC-1
Morphogens
    Bone morphogenic proteins (BMPs)
Nitric oxide (NO)
Nucleotides
Peptides
PR39
Proteins
Prostaglandins
Proteoglycans
Perlecan
Radioactive materials
    Iodine - 125
    Iodine - 131
    Iridium - 192
    Palladium 103
    Radio-pharmaceuticals
Secondary Messengers
    Ceramide
Signal Transduction Factors
Signaling Proteins
Somatomedins
Statins
Stem Cells
Steroids
Thrombin TABLE 3-continued Examples with Some Types of Biological, Pharmaceutical, and other Therapies that can be Delivered via the Composite Device in Accordance with the Present Invention Sulfonyl
Thrombin inhibitor
Thrombolytics
Ticlid
Tyrosine kinase Inhibitors
    ST638
    AG-17
Vasodilator
    Histamine
    Forskolin
    Nitroglycerin
Vitamins
    E
    C
Yeast Therapy delivery may come from the pores 14 of the composite prosthesis 51, as released from physical entrapment of the therapy impregnated within the walls of the pores 14; it may come from material adsorbed or loosely adhering to the surface of enclosed pores 14 or interconnected pores (not shown); or it may stay suspended within the pores 14 of the composite device 51 as implanted, awaiting contact with tissue fluid entering the pores 14. FIG. 5 depicts the composite prosthesis 51 having irregular, random pores, it is recognized that a composite prosthesis having regular, ordered pores and additional material would behave similarly.

It is recognized that each of the delivery modes could result in different delivery rates. That is, therapy may evolve more rapidly from interconnected pores (not shown), than from isolated pores 14, which may in-turn release therapy faster than any therapy delivered by the polymer constituent (e.g., as it degrades).

In one embodiment the therapy delivered via the additional material 50 is co-mingled with the various other constituents and components prior to the processing. This allows for some concentration of the therapy to remain in the polymer constituent, while some of the same therapy migrates or precipitates into the porous region of the matrix. An equilibrium phase diagram for the components and constituents would allow the tailoring of the concentration of therapy in each region (i.e., pore or polymer constituent), additionally, therapies with low solubility in either component will aid preferential placement of therapy.

Figure 6B:
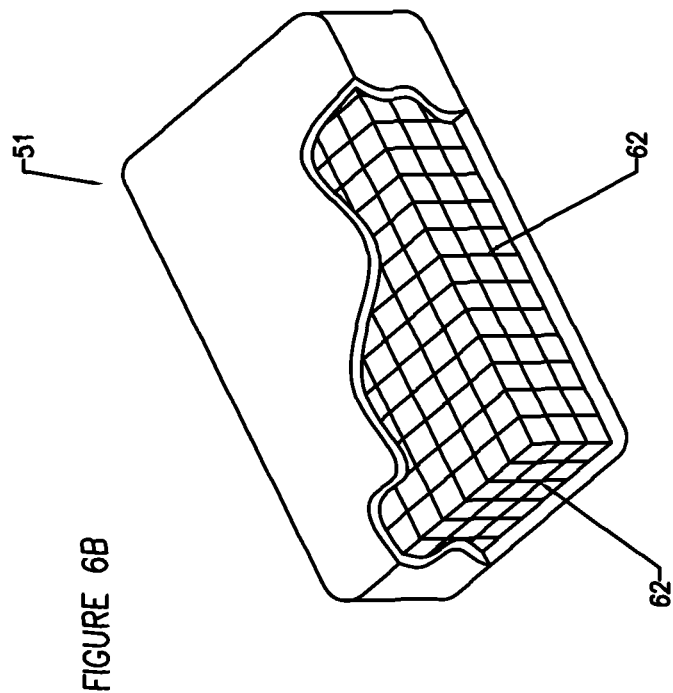
FIG. 6 (a) Cutaway perspective view of the prosthesis bone plate having at least one reinforcing fiber arranged randomly throughout the prosthesis; (b) cutaway perspective view of the prosthesis bone plate having a reinforcing weave or mesh. For simplicity of drawing, the porous nature of the material is not depicted.
Figure 6A:
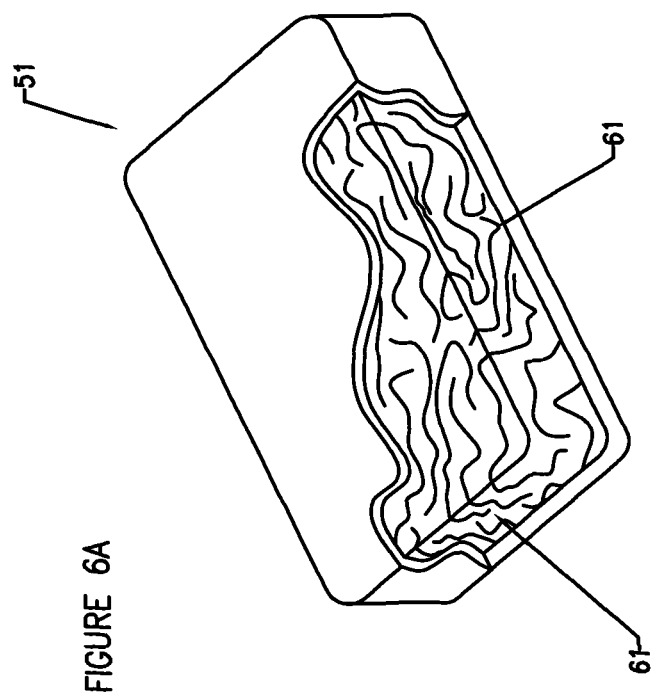

As shown in FIG. 6*a*, an alternative embodiment of the composite prosthesis 51 may also incorporate random fibers or whiskers 61 as the additional material to add strength or another property to the composite prosthesis 51. Alternatively, and as shown in FIG. 6*b*, the fibers may be arranged in a non-random pattern, such as a weave, knit or mesh, or scaffold 62. The patterned fibers 62 may be arranged in a single layer forming a two-dimensional sheet, or they may form a reinforcing scaffold extending in three dimensions through the composite prosthesis 51. The patterned fibers 62 or the random fibers 61, may extend throughout the entirety of the composite prosthesis 51, or alternatively may be limited to a particular portion or layer of the composite prosthesis 51, where greater strength or altered physical characteristic is desired.

The incorporation of random fibers 61 or a non-random pattern of fibers 62 into the porous material of the composite prosthesis 51 may impart additional shear strength to the implant, enabling it to further resist mechanical stresses imposed while implanted in the living being. The fibers 61, 62 may also serve as an additional safety measure; upon the formation of a break or fault in the porous structure of the implant, the incorporated fibers would ensure that the entire prosthesis is able to remain in place, preventing a loose piece of the implant from being able to migrate within the being.

The random fibers or whiskers 61, or the non-random fibers 62, comprising the additional material may be biocompatible and non-resorbable, or more preferably biocompatible and resorbable, such that as the porous material of the composite device 51 is absorbed by the living being, the fibers 61, 62 are absorbed as well. Resorbable fibers comprising the additional material may be constructed from materials selected from table 1 above, a non-exhaustive list of some of the materials from which the resorbable prosthesis may be constructed. The fibers 61, 62 may be the same material or a different material from the porous material comprising the prosthesis. Depending on the materials selected, the composite prosthesis 51 may be resorbed at the same rate or a different rate from the incorporated fibers 61, 62.

The structure of the prosthesis may be manufactured in such a way that there is a layered appearance to the bone plate when viewed in cross-section. This may be accomplished by methods commonly known in the art, such as: porosogen particulate leaching; blown gas methods; gas forming polymerizations; lyophilization; phase separation, as described in U.S. Pat. No. 6,355,699 B1 (Vyakarnum), and U.S. patent application Ser. No. 10/022,182 (Bowman). Any of these methodologies may be utilized to create a prosthesis entirely uniform in material, however, having layers with a variety of pore sizes and densities (not shown). For example, there may be a first layer of material that is relatively less porous, transitioning through a first interface to a layer that is relatively more porous, and transitioning through a second interface to a layer that is relatively less porous. By tailoring the manufacturing process, a great many variety of combinations may be constructed into a prosthesis.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A bendable polymer tissue fixation device for implantation into a living body, said polymer fixation device comprising a laminar body having an first layer, a second layer and an interface, said first layer comprising a porous form of a polymer material, said second layer comprising a non-porous form of said polymer material; said polymer material comprising a biopolymer, said porous form transitioning to the non-porous form at said interface, wherein at least at room temperature and within a period of time that is from prior to said implantation up through said implantation, said laminar body possesses the following properties: being capable of being smoothly bent upon application of a bending force, the bending force permanently collapsing a portion of the pores of the porous form to prevent cracking or breaking of the non-porous form, and said laminar body maintaining said bent condition following removal of the bending force.

2. The polymer tissue fixation device of claim 1 wherein the porous body can be smoothly bent to conform to a tissue structure, said smooth bending being capable of occurring at a temperature below the glass transition point of the polymer.

3. The polymer tissue fixation device of claim 1 wherein the porous body comprises a plurality of porous zones, wherein at least one zone of pores is less able to withstand compressive force than other zones.

4. The polymer tissue fixation device of claim 3 wherein the porous body can be compressed against an irregular surface, whereupon less than all of the pores collapse, and the device conforms to the irregular surface.

5. The polymer tissue fixation device of claim 1 wherein the pores are arranged to yield and selectively collapse to allow for placement of a fastening device to fasten the polymer fixation device within the living body.

6. The polymer tissue fixation device of claim 1 wherein the porous body is capable of being fastened within the living body by one or more means selected from the group consisting of adhesive, wire, staple, suture, pin, nail, tack, screw, and a clamp.

7. The polymer tissue fixation device of claim 1 further comprising a plurality of holes extending through the prosthesis, said plurality of holes serving as a fastening location.

8. The polymer tissue fixation device of claim 1 wherein the porous body further comprises additional material.

9. The polymer tissue fixation device of claim 8 wherein the additional material further comprises biologically active agents.

10. The polymer tissue fixation device of claim 9 wherein at least a portion of said biologically active agent is located within a least a portion of the pores.

11. The polymer tissue fixation device of claim 9 wherein at least a portion of said biologically active agent is located within the polymer of said polymer fixation device.

12. The polymer tissue fixation device of claim 8 wherein the additional material further comprises particulate material, said particulate material having a property selected from the group consisting of biologically active agent delivery, tissue fixation device rigidity enhancement, radiopacity, or microspheres.

13. The polymer tissue fixation device of claim 8 wherein the additional material is one of distributed evenly throughout the device, or distributed unevenly throughout said device.

14. The polymer tissue fixation device of claim 8 wherein the additional material serves to alter the rate of resorption of the polymer fixation device.

15. The polymer tissue fixation device of claim 1, wherein the porous body is capable of being smoothly bent without the need for one of heating or special tools.

16. A bendable polymer tissue fixation device for implantation into a living body, said polymer fixation device comprising a laminar body having an first layer, a second layer and an interface, said first layer comprising a porous form of a first polymer material, said second layer comprising a non-porous form of a second polymer material; said first and second polymer materials comprising biopolymers, said porous form comprising a plurality of pores, said porous form transitioning to the non-porous form at said interface, wherein at least at room temperature and within a period of time that is from prior to said implantation up through said implantation, said laminar body intrinsically is capable of being smoothly bent by a bending force that irreversibly collapses a portion of the pores of the porous form to prevent cracking or breaking of the non-porous form, and wherein said laminar body intrinsically maintains said bent condition following removal of the bending force.

17. The polymer tissue fixation device of claim 16 wherein the porous body can be smoothly bent to conform to a tissue structure, said smooth bending being capable of occurring at a temperature below the glass transition point of the polymer.

18. The polymer tissue fixation device of claim 16 wherein the porous body comprises a plurality of porous zones, wherein at least one zone of pores is less able to withstand compressive force than other zones.

19. The polymer tissue fixation device of claim 18 wherein the porous body can be compressed against an irregular surface, whereupon less than all of the pores collapse, and the device conforms to the irregular surface.

20. The polymer tissue fixation device of claim 16 wherein the pores are arranged to yield and selectively collapse to allow for placement of a fastening device to fasten the polymer fixation device within the living body.

21. The polymer tissue fixation device of claim 16 wherein the porous body is capable of being fastened within the living body by one or more means selected from the group consisting of adhesive, wire, staple, suture, pin, nail, tack, screw, and a clamp.

22. The polymer tissue fixation device of claim 16 further comprising a plurality of holes extending through the prosthesis, said plurality of holes serving as a fastening location.

23. The polymer tissue fixation device of claim 16 wherein the porous body further comprises additional material.

24. The polymer tissue fixation device of claim 23 wherein the additional material further comprises biologically active agents.

25. The polymer tissue fixation device of claim 24 wherein at least a portion of said biologically active agent is located within a least a portion of the pores.

26. The polymer tissue fixation device of claim 24 wherein at least a portion of said biologically active agent is located within the polymer of said polymer fixation device.

27. The polymer tissue fixation device of claim 23 wherein the additional material further comprises particulate material, said particulate material having a property selected from the group consisting of biologically active agent delivery, tissue fixation device rigidity enhancement, radiopacity, or microspheres.

28. The polymer tissue fixation device of claim 23 wherein the additional material is one of distributed evenly throughout the device, or distributed unevenly throughout said device.

29. The polymer tissue fixation device of claim 23 wherein the additional material serves to alter the rate of resorption of the polymer fixation device.

30. The polymer tissue fixation device of claim 16, wherein the porous body is capable of being smoothly bent without the need for one of heating or special tools.

* * * * *